Figure 1:
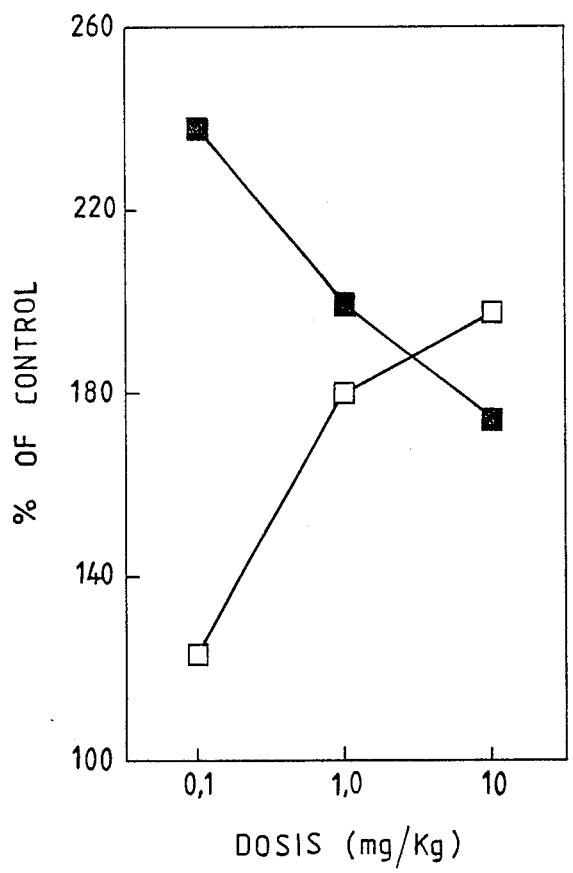

United States Patent [19]

Nencioni et al.

[11] Patent Number: 4,957,736

[45] Date of Patent: Sep. 18, 1990

[54] COMPOSITION FOR VACCINES

[75] Inventors: Luciano Nencioni, Poggibonsi; Piero Pileri, Monteriggioni; Samuele Peppoloni, Perugia; Sergio Silvestri, Siena, all of Italy

[73] Assignee: Sclavo S.p.A., Siena, Italy

[21] Appl. No.: 357,267

[22] Filed: May 26, 1989

[30] Foreign Application Priority Data

Feb. 10, 1989 [IT] Italy .................. 19408 A/89

[51] Int. Cl.[5] .................. A61K 39/002; A61K 39/02; A61K 39/10; A61K 39/12
[52] U.S. Cl. .................. 424/88; 424/89; 424/90; 424/91; 424/92; 530/328; 530/330
[58] Field of Search .................. 530/328, 330; 424/89, 424/92, 88, 90, 91

[56] References Cited

U.S. PATENT DOCUMENTS 4,353,823 10/1982 Chipens et al. .................. 530/330
4,390,528 6/1983 Najjar .................. 530/328

*Primary Examiner*—Lester L. Lee
*Attorney, Agent, or Firm*—Oblon, Spivak, McClelland, Maier & Neustadt

[57] ABSTRACT

The invention is concerned with the use of a compound analogous to tuftsin, having the formula (I)

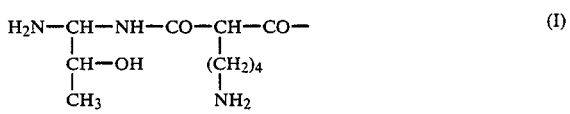

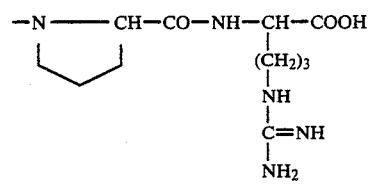

or of a pharmaceutically acceptable base-addition or acid-additon salt thereof, as an adjuvant in order to potentiate, in a living organism, the antibody response against either natural or synthetic antigens, as well as with the novel compositions for vaccines which comprise one or more of said antigens together with an adjuvating amount of the compound of formula (I) or of one of its addition salts.

5 Claims, 4 Drawing Sheets

COMPOSITION FOR VACCINES

The present invention relates to the use of a retroinverse compound analogous of tuftsin of formula (I)

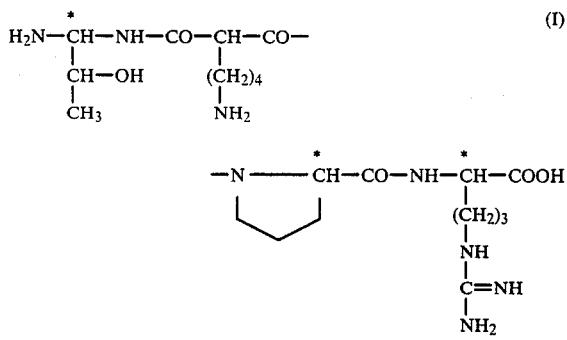

wherein the absolute configuration of the carbon atoms marked by means of the asterisks is the L-configuration, and the absolute configuration of the carbon atom of the malonyl residue may be either the L- or the D- configuration, or of a pharmaceutically acceptable base-addition or acid-addition salt thereof, as an adjuvant in order to potentiate, in a living organism, the antibody response against either natural or synthetic antigens, as well as to the compositions for vaccines which contain one or more of said antigens together with an adjuvating amount of the compound of formula (I) or of one of its addition salts.

By the term "antigen", any substance is meant, which is foreign to a living organism and, once that it comes into contact with the immunitary system, activates a complex series of cellular interactions aiming at eliminating the same antigen and at establishing again the pre-existing equilibrium. Typical features for an antigen are the immunogenicity, i.e., its ability to induce the formation of specific antibodies, and the antigenicity, i.e., its ability to be selectively recognized by the antibodies it induced.

In most cases, the reactivity of a living organism following an antigenic stimulation can depend, besides on the administration way, also on the used antigen dose. Furthermore, some antigens, even when used at high doses, show a low degree of immunogenicity; i.e., they induce an antibody response which is not enough in order to give the organism an efficacious protection. This is particularly true for those antigens which are used in the preparation of vaccines of last generation, i.e., the vaccines of synthetic type, or those obtained by means of the technique of recombinant DNA.

The immunogenicity of an antigen can anyway be improved by administering said antigen together with substances, called "adjuvants", which potentiate the antibody response to the antigen either by directly acting on the immunitary system, or by modifying the pharmaco-kinetic properties of the antigen, so as to increase its time of interaction with the immunitary system.

The most commonly used adjuvant in the preparation of vaccines for use in human therapy is alum, or aluminum hydroxide. Such an adjuvant is both capable of prolonging the time of permanence of the antigen inside the organism, and of generating a non-specific activation of the immunitary system. However, the presence of possible undesirable side effects, such as the arising of burning sensation or of acute pain, in addition to the poor efficacy towards determined synthetic antigens and thymus-depending antigens, render the use of aluminum hydroxide not completely satisfactory. The need therefore derives for having available substances which are capable of potentiating in vivo the immunitary response to determined antigens, which are free from the drawbacks which affect the prior art.

The present Applicant has found now that the compound of formula (I)

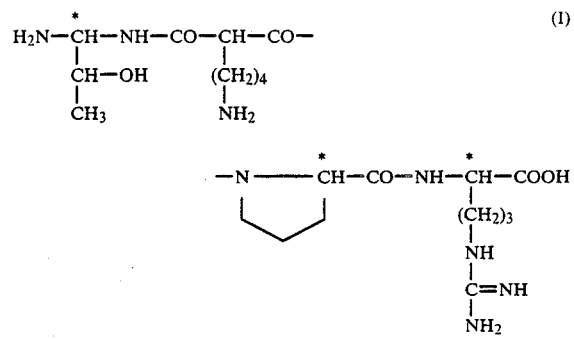

is capable, when is administered to an animal before, or simultaneously to, one or more either natural or synthetic antigen(s), of potentiating to a meaningful extent its antibody response, without causing undesired side effects.

In the above reported formula (I), the absolute configuration of the carbon atoms marked with an asterisk is the L-configuration, and the absolute configuration of the carbon atom of the malonyl residue can be either the L- or the D-configuration.

In particular, the compound with which the experimental tests were carried out, is a mixture of the two diastereoisomers having L-configuration at asymmetrical carbon atoms of the first, third and fourth aminoacidic or pseudo-aminoacidic residues of the sequence, starting from the N-terminal residue (the carbon atoms marked with the asterisk), and either D- or L-configuration at the asymmetrical carbon atom of the malonyl residue.

The compound of formula (I) is a retro-inverse compound analogous of tutsin, disclosed in European patent application publ. No. 253,190.

Tuftsin is a tetrapeptide, containing the

Thr-Lys-Pro-Arg sequence, isolated in 1970 by a group of U.S. researchers. It is cleft from a particular immunoglobulin, leucokinin, by the action of two enzymes, tuftsin-endocarboxy-peptidase, an enzyme to be found in spleen, which acts on circulating leucokinin, cleaving the Arg-Glu link and thus liberating the carboxy chain end of tuftsin, and leucokinase, a membrane enzyme of neutrocytes, monocytes and macrophages (MO), which cleaves the Lys-Thr link, thus liberating the aminic chain end of tuftsin.

The main biological effect of tuftsin is of potentiating a number of functions of polymorphonuclear granulocytes and tissular macrophages, with it performing its activity only when is liberated from the carrier leucokinin molecule. Inasmuch as the macrophages, besides being phagocytic cells, play a fundamental role also as accessory cells, i.e., cells destined to the "presentation of the antigen" by interacting with the lymphocytes, tuftsin is likely to be able to influence the reactivity of the host organism by acting as a pleiotropic immunomodulator of several components of the immune system.

Tuftsin forms a bond with specific receptors existing on the plasmatic membrane of phagocytic cells, then passes through the membrane and in cytoplasm is metabolized by some cytoplasmatic enzymes. The most active one of such enzymes is an aminopeptidase which cleaves the threonine residue, forming the Lys-Pro-Arg tripeptide, which is a powerful inhibitor of the activity of tuftsin.

As disclosed in the above cited European patent application, the compound of formula (I), which can also be indicated in short form by means of a terminology recognized at the international level:

gThr-mLys-Pro-Arg-OH wherein the "g" character immediately before the designation of threonine aminoacid means that such an aminoacidic residue was converted into its corresponding gem-diamino-alkyl derivative; and the "m" character immediately before the designation of lysine aminoacid means that such an aminoacidic residue was converted into its corresponding malonyl derivative, showed to be endowed with substantially the same pharmacological activities of tuftsin, anyway associated with a better stability to plasmatic peptidases.

But, differently from tuftsin, which is capable of potentiating in vivo the antibody response to a determined antigen only when it is administered, at suitable dosages, some days prior to the administration of the same antigen, the compound of formula (I), as well as its pharmaceutically acceptable base-addition salts or acid-addition salts, are capable of potentiating the primary antibody response against a thymus-depending agent both when they are administered a few days prior to, and simultaneously to, the same antigen.

The present invention makes it therefore possible vaccines to be formulated which, with one single administration, induce efficacious specific antibody responses with lower doses of immunogenic antigens, or which, with the dose of antigens—in particular of poorly immunogenic antigens—being the same, offer a more complete immunization with one single administration.

The compound of formula (I), as well as its pharmaceutically acceptable acid-addition or base-addition salts thereof can be used in order to formulate either bacterial or viral vaccines, containing one or more antigens of proteinic, polysaccharidic, or glycoproteinic structure. In the preparation of such vaccines containing a plurality of antigens, such antigens can be used in order to induce immunization against a same disease, or a plurality of diseases (polyvalent vaccines). Furthermore, the compound of formula (I), which showed to be endowed with a potentiating activity for the primary antibody response also when is administered by oral way can be also used, with suitable antigens, for the preparation of oral vaccines. The methods for obtaining either natural or synthetic antigens, as well as the techniques of preparation of such compositions, substantially are those already known in the field.

Such vaccines are generally prepared by freeze-drying, either separately or jointly, the antigen and the adjuvant of formula (I) in the suitable doses and reconstituting the vaccine at use time with a suitable aqueous carrier (distilled water, physiologic solution, suitable buffers). Such a vaccine can also contain other ingredients, such as stabilizers, preservatives, and so forth. In case of oral formulations, such a vaccine may also contain flavouring agents, as known in pharmaceutical technique, with the whole being formulated as gastro-resistant dosage forms, typically gastro-resistant capsules, in order to prevent the active substances from undergoing denaturation and enzymatic degradation at gastric level.

In general, the used doses of antigen are lower than, or equal to, those as conventionally used; on the contrary, as regards the adjuvant of formula (I), doses generally comprised within the range of from 1 µg to 1 mg/kg, according to the administration way and of the particular type of antigen used, produce the desired immunopotentiating effects.

Vaccines which can be well prepared by using the compound of formula (I) as an adjuvant are, e.g., cell-free vaccines against pertussis, to be developed in future; A, B and C meningococcal vaccines; polysaccharide pneumococcal vaccines; diphteric and tetanic vaccines; recombinant vaccines and plasma-derived vaccines against hepatitis, besides cell-free vaccines against cholera, to be administered by oral way as gastro-resistant forms, and still other similar vaccines.

The following Example is supplied for the only purpose of better illustrating the present invention, and should not be construed as being limitative of the scope of the same invention.

EXAMPLE 1

Effect on the Primary Antibody Response against a Thymus Depending Antigen

The ability of the compound of formula (I) (obtained as disclosed in Example 1 of EP-A No. 253190) to stimulate the primary antibody response against red cells of ram (SRBC), a thymus-depending antigen, was evaluated by means of the method of plaques of hemolysis described by Cunningham and Szenberg [Immunology 14, 599 (1968)]. This method makes it possible the number of cells secreting specific anti-SRBC antibodies to be determined, and consists in immunizing mice with SRBC, in contacting the lymphocytes obtained from the spleen of these immunized mice with the same antigen used for immunization and finally evidencing the hemolytic plaques by means of the addition of complement.

At those sites where the antigen-antibody reaction took place, i.e., in correspondence of each cell producing specific anti-SRBC antibodies, the formation of areas of lysis is observed (plaque forming cells - PFC).

By means of this method—called the "direct method"—the cells are evidenced which secrete antibodies of IgM class, typical for the primary antibody response against the immunization agent.

The cells secreting antibodies of IgM class were determined by isolating the lymphocytes from the spleen of rats immunized with the SRBC antigen, and treated according to different modalities, and with different doses of compound of formula (I).

SRBC antigen, before being inoculated into the mice by intravenous way, is washed and suspended in apyrogenetic saline solution.

On the contrary, the compound of formula (I) was administered to the test animals, as a single dosis, both by oral and intravenous way, either separately from or simultaneously with the antigens, at concentrations comprised within the range of from 0.001 to 10 mg/kg per dose, as a sterile solution in physiologic solution. The resulting solution, before being inoculated into the mice, was adjusted at a neutral pH.

In parallel, the same group of tests was carried out by using tuftsin in lieu of the compound of formula (I).

The possible immunostimulating activity is evidenced on the basis of the cells which secrete antibodies of IgM class, determined as PCF's/spleen 4 days after the immunization.

(a) Determination of the immunostimulating effect of the compound of formula (I) as compared to tuftsin, administered by intravenous way 7 days before the antigen Groups consisting of three C3H/HeNCr1BR inbred male mice of 10–12 weeks of age and having a body weight of about 25 g are treated by intravenous way on day −7 with an apyrogenic saline solution (0.2 ml) either alone, or containing 0.1, 1.0 and 10 mg/kg of the compound of formula (I), or of tuftsin. On day 0, all mice are treated, still by intravenous way, with 0.2 ml of saline solution containing 2–3×10$^8$ red cells of ram (SRBC - Sclavo). Four days later, all mice are sacrificed and their spleen is drawn and mechanically dissociated in order to separate the lymphocytes. The so isolated lymphocytes are washed with minimum medium containing Earle salts (M.E.M. - MA Bioproducts) (3×15 ml) and are then suspended again in the same medium (1 ml) at an end concentration of 150,000 cells. A sample (100 μl) of each cellular suspension is subsequently diluted 1:100 with M.E.M. medium and 100 μliters of each dilution are charged to wells of microplates (two samples are run per each dilution), with each well containing 25 μl of M.E.M. medium, 25 μl of a suspension at 10% of SRBC and 25 μl of Guinea pig complement to an end dilution of 1:64. The whole suspension is immediately transferred by capillarity from each well onto superimposed glass slides.

The slides, sealed along their edges with paraffin, are then incubated inside a thermostatic oven, at 37° C. for one hour. At the end of this time, by means of a light-contrast viewer, the direct plaques of hemolysis are counted, which indicate the number of antibody secreting lymphocytes (PFC).

The so evidenced antibodies belong to IgM class, typical for the primary antibody response. The effect of immunostimulation on the primary response to SRBC, measured as direct PFC's/spleen is shown in FIG. 1, expressed as the percent value relatively to the response of control animals which receive only antigen. Such results show that the compound of formula (I) (■—■) is endowed with a considerably high immunostimulating activity even at doses which are up to 100 times lower than the active doses of tuftsin (□—□).

Statistical significance of the data reported in FIG. 1:
tuftsin 0.1 mg/kg vs. control: not significant;
all other groups vs. control: $p<0.01$;
compound of formula (I) 0.1 mg/kg vs. tuftsin 0.1 mg/kg: $p<0.01$;
all other groups of compound of formula (I) vs. corresponding tuftsin groups: not significant.

(b) Determining of the immunostimulating effect of the compound of formula (I) as compared to tuftsin, when administered by intravenous way together with the antigen Groups of three mice each are treated by intravenous way on day 0 with a saline solution (0.4 ml) containing 2–3×10$^8$ SRCB, or with a saline solution (0.4 ml) containing 2–3×10$^8$ SRCB and 0.001, 0.01, 0.1, 1.0 and 10 mg/kg of compound of formula (I) or of tuftsin. After 4 days of the administration, the test of the hemolysis plaques is carried out according to the same methodology as hereinabove disclosed.

Figure 2:
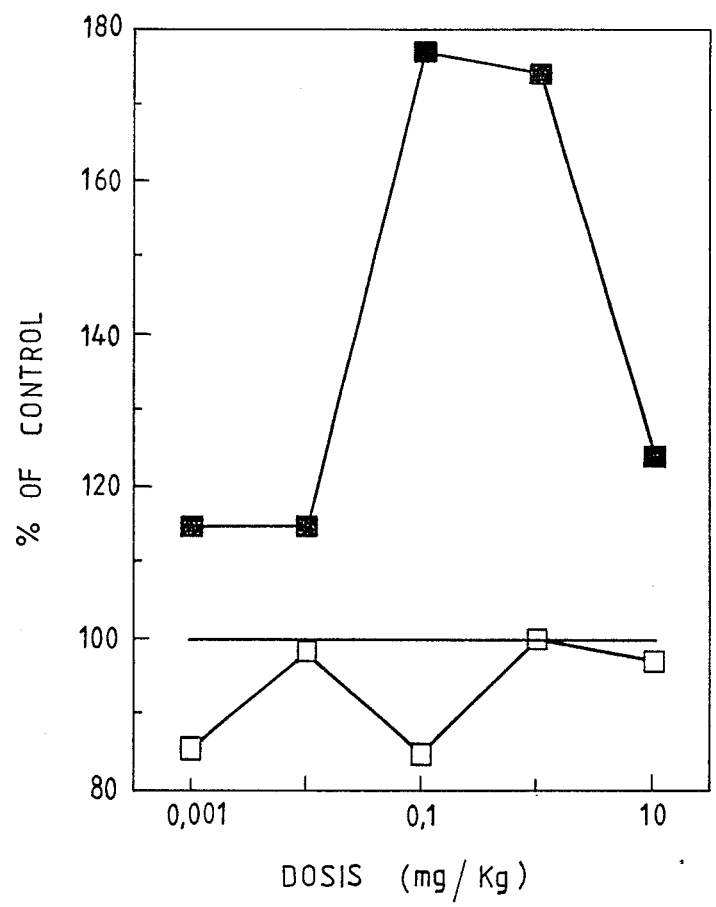

The results, reported in FIG. 2, and expressed in the same way as described for FIG. 1, show a significant immunostimulating activity of the compound of formula (I) (■—■), depending on the dose, and maximum at 0.1 mg/kg, whilst, as also reported in the relevant literature (Florentin et al., 1983), tuftsin (□—□) is never active under these conditions.

Statistical significance of the data reported in FIG. 2:
all tuftsin groups vs. control: not significant;
compound of formula (I) 0.1 and 1.0 mg/kg vs. control: $p<0.01$;
all other groups vs. control: not significant.

(c) Determination of the immunostimulating effect of the compound of formula (I) as compared to tuftsin, when administered by oral way 7 days before the inoculation of the antigen by intravenous way Groups of three mice each are treated by oral way (intragastric intubation) on day −7 with an apyrogenic saline solution (0.2 ml) either alone, or containing 0.01, 0.1, and 0.1 mg/kg of compound of formula (I) or of tuftsin. On days 0 all mice are treated by intravenous way with a saline solution (0.2 ml) containing 2–3×10$^8$ SRBC. Four days later the test of the hemolysis plaques is carried out according to the usual method.

Figure 3:
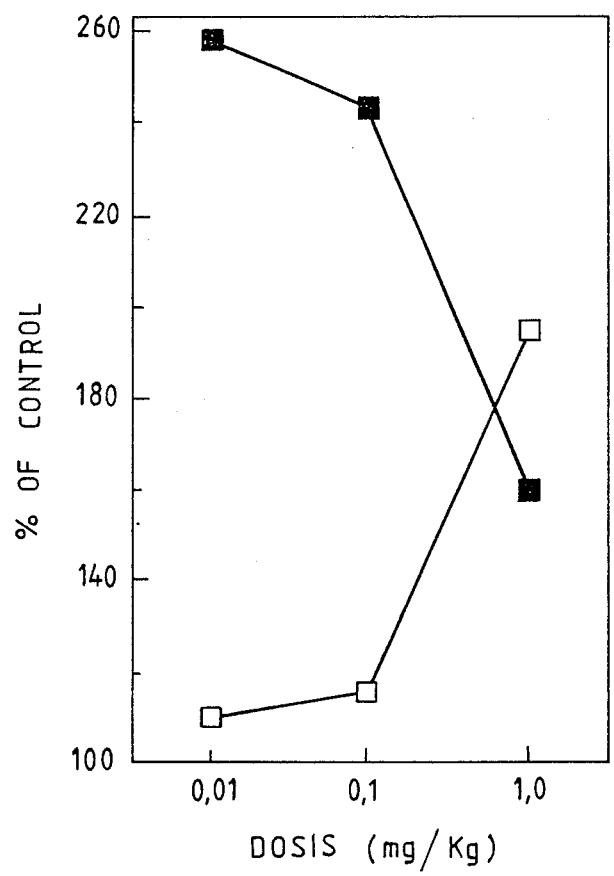

The results, reported in FIG. 3, and expressed in the same way as described for FIG. 1, show a considerable immunostimulating activity of the compound of formula (I) (■—■) at all tested doses (with a peak at 0.01 mg/kg), whilst tuftsin (□—□) results to be active only at 1.0 mg/kg.

Statistical significance of the data reported in FIG. 3:
tuftsin 0.01 and 0.1 mg/kg vs. control: not significant;
tuftsin 1 mg/kg vs. control: $p>0.01$;
all groups of compound of formula (I) vs. control: $p>0.01$;
compound of formula (I) 0.01 and 0.1 mg/kg vs. corresponding tuftsin groups: $p<0.01$.
compound of formula (I) 1 mg/kg vs. tuftsin 1 mg/kg: not significant.

(d) Determination of the immunostimulating effect of the compound of formula (I) as compared to tuftsin, when administered by oral way on the same day as of the inoculation of the antigen by intravenous way Groups of three mice each are treated by intravenous way with a saline solution (0.2 ml) containing 2–3×10$^8$ SRBC, and then by oral way with a saline solution (0.2 ml) either alone or containing 0.01, 0.1, 1.0 and 10 mg/kg of compound of formula (I) or of tuftsin. After 4 days of the administration, the test of hemolysis plaques is carried out according to the same methodology as hereinabove disclosed.

Figure 4:
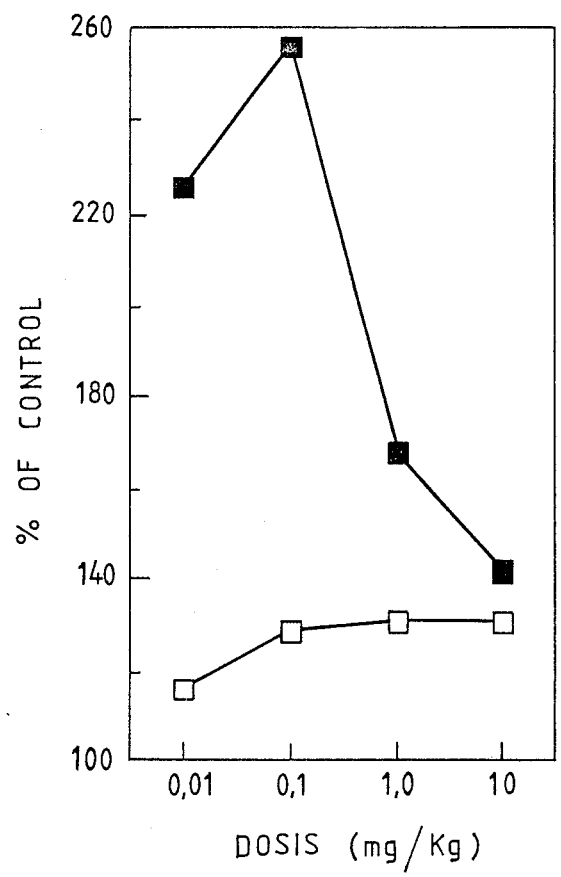

The results, reported in FIG. 4, and expressed in the same way as described for FIG. 1, demonstrate the ability of the compound of formula (I) (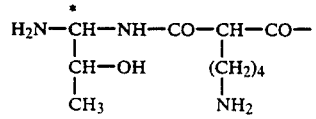) to induce a significant increase in anti-SRBC primary response, at all tested doses, and with a maximum at 0.01 mg/kg, whilst tuftsin ( ) is never active under these conditions.

Statistical significance of the data reported in FIG. 4:

all tuftsin groups vs. control: not significant;

all groups of compound of formula (I) vs. control: p<0.01;

compound of formula (I) 0.01 and 0.1 mg/kg vs. the corresponding groups of tuftsin: p<0.01.

Compound of formula (I) 1 and 10 mg/kg vs. the corresponding tuftsin groups: p<0.03.

We claim:

1. A vaccine comprising one or more antigens of either natural or synthetic origins, together with an adjuvant amount of a compound of formula (I)

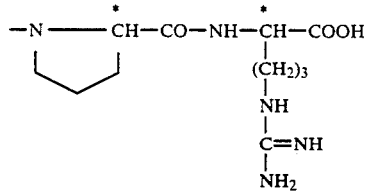

wherein the absolute configuration of each carbon atom marked with an asterisk is the L-configuration, and the absolute configuration of the carbon atom of the malonyl residue is either the L- or the D-configuration; or with a pharmaceutically acceptable base-addition or acid-addition salt thereof.

2. Vaccine according to claim 1 wherein the antigen is of proteinic or glyco-proteinic type.

3. Vaccine according to claim 1 wherein as the adjuvant a mixture is used of diastereoisomers having absolute L-configuration at the carbon atoms marked with an asterisk, and L- and D-configuration at the asymmetrical carbon atom of the malonyl residue.

4. A vaccine comprising one or more antigens of either natural or synthetic origin derived from at least one member of the group consisting of pertussis, A, B and C meningitis, polysaccharide pneumococci, diphtheria, tetanus, hepatitis and chlorera; together with an adjuvant amount of a compound of formula (I)

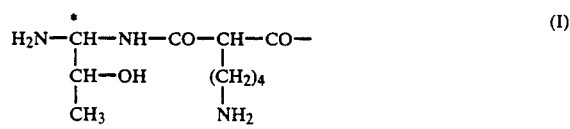

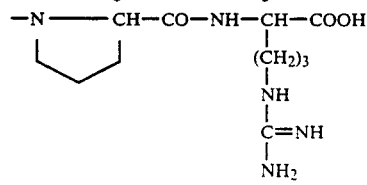

wherein the absolute configuration of each carbon atom marked with an asterisk is the L-configuration and the absolute configuration of the carbon atom of the malonyl residue is either the L- or the D-configuration or with a pharmaceutically acceptable base-addition or acid-addition salt thereof.

5. The vaccine according to claim 4 wherein as the adjuvant a mixture is used of diastereoisomers having absolute L-configuration at the carbon atoms marked with an asterisk, and L- and D-configurations at the asymmetrical carbon atom of the malonyl residue.

* * * * *